(12) United States Patent
Moon et al.

(10) Patent No.: US 9,352,970 B2
(45) Date of Patent: May 31, 2016

(54) METHOD FOR PRODUCING SILICON FOR SOLAR CELLS BY METALLURGICAL REFINING PROCESS

(75) Inventors: Byung Moon Moon, Seoul (KR); Tae U Yu, Seoul (KR); Dong Ho Park, Gyeonggi-do (KR); Hyun Jin Koo, Gyeonggi-do (KR); Gang June Kim, Gyeonggi-do (KR); Eun Su Jang, Jeonbuk (KR); Sang Wook Lee, Chungcheongnam-do (KR)

(73) Assignee: KOREA INSTITUTE OF INDUSTRIAL TECHNOLOGY, Chungcheongnam-do (KR)

(*) Notice: Subject to any disclaimer, the term of this patent is extended or adjusted under 35 U.S.C. 154(b) by 8 days.

(21) Appl. No.: 14/380,239

(22) PCT Filed: Jun. 28, 2012

(86) PCT No.: PCT/KR2012/005138
§ 371 (c)(1),
(2), (4) Date: Dec. 8, 2014

(87) PCT Pub. No.: WO2013/125756
PCT Pub. Date: Aug. 29, 2013

(65) Prior Publication Data
US 2015/0135770 A1    May 21, 2015

(30) Foreign Application Priority Data
Feb. 21, 2012  (KR) .................. 10-2012-0017583

(51) Int. Cl.
*C01B 33/039* (2006.01)
*C01B 33/037* (2006.01)
*C07C 29/74* (2006.01)
*C01B 33/025* (2006.01)

(52) U.S. Cl.
CPC .............. *C01B 33/039* (2013.01); *C01B 33/037* (2013.01); *C07C 29/74* (2013.01); *C01B 33/025* (2013.01)

(58) Field of Classification Search
CPC .. C01B 33/021; C01B 33/025; C01B 33/037; C01B 33/039
See application file for complete search history.

(56) References Cited

U.S. PATENT DOCUMENTS

| 2010/0233063 A1 | 9/2010 | Chou |
| 2011/0142724 A1 | 6/2011 | Moon et al. |

FOREIGN PATENT DOCUMENTS

| JP | 2009-114026 | 5/2009 |
| JP | 2010-215485 | 9/2010 |
| KR | 10-2011-0004129 | 1/2011 |
| KR | 10-2011-0050371 | 5/2011 |

OTHER PUBLICATIONS

International Search Report for PCT/KR2012/005138 mailed Jan. 23, 2013, 4 pages.

*Primary Examiner* — Anthony J Zimmer
(74) *Attorney, Agent, or Firm* — Nixon & Vanderhye P.C.

(57) ABSTRACT

In order to produce metallurgical grade silicon and solar cell grade polysilicon in batches, a method of the present invention comprises: a step of reduction in an arc furnace, consisting of removing C and CO in a silicon reduction atmosphere using silica stone and carbon black by an arc so as to produce metallurgical grade silicon; a step of refining by slag consisting of removing phosphorus (P) and boron (B) by slag; a step of refining by unidirectional solidification consisting of removing metal impurities (Fe, Al, Ti, Mn, etc.) by means of unidirectional solidification; and a step of steam plasma-electromagnetism continuous refining consisting of charging a furnace with the unidirectionally solidified silicon and removing boron (B) by a steam plasma torch.

6 Claims, 5 Drawing Sheets

METHOD FOR PRODUCING SILICON FOR SOLAR CELLS BY METALLURGICAL REFINING PROCESS

This application is the U.S. national phase of International Application No. PCT/KR2012/005138 filed 28 Jun. 2012 which designated the U.S. and claims priority to Korean Patent Application No. KR10-2012-0017583 filed 21 Feb. 2012, the entire contents of each of which are hereby incorporated by reference.

TECHNICAL FIELD

The present invention relates to an apparatus and method of producing silicon for solar cells from silica stone. More particularly, the present invention relates to an apparatus and method for producing silicon for solar cells, in which metallurgical-grade silicon (MG-Si) is produced from silica stone in a molten state, and silicon suitable for use in solar cells is produced from the molten metallurgical-grade silicon by a metallurgical process, and thus the consumption of energy, the production cost of silicon and the occurrence of environmental pollution can be reduced.

BACKGROUND ART

The solar cell market has grown rapidly at a rate of 35% or higher since 2003. The price of polysilicon that is the main material of solar cells temporarily declined in the first half of 2009 and has shown an upward tendency since 2010, but it is predominantly expected that the price of polysilicon will be stabilized at low prices in the future. Thus, the development of a technology for producing highly pure inexpensive polysilicon can lead to increases in competitiveness and market share in the global polysilicon market and will have a great ripple effect on the related industries.

Among current commercial technologies for producing silicon for solar cells, the so-called Siemens process that is a vapor-phase process is most frequently used. This vapor-phase process that comprises reacting metallurgical-grade silicon (MG-Si), produced from silica stone, with HCl or $H_2$ to make a gaseous mixture, purifying the gaseous mixture in a distillation column to remove impurities, and depositing high-purity polysilicon from the resulting silicon rod. This vapor-phase process can be applied to both the semiconductor industry and the solar cell industry, because it can produce high-quality polysilicon. However, the vapor-phase process requires large-scale investment (an equipment investment of about one hundred million Won (Korean currency) per ton of production of polysilicon) and high energy consumption (about 120 kWh/kg), and thus when it is applied to the solar cell industry, it can be a highly expensive process.

For this economic reason, technology for a metallurgical refining process, but not the vapor-phase process, has recently been developed. As used herein, the term "metallurgical refining process" refers to a process of refining metallurgical-grade silicon by slag treatment, segregation, rapid solidification, electron beams, plasma, etc. The metallurgical refining process has advantages in that it can produce polysilicon using energy of ⅓ compared to the vapor-phase process and can reduce the occurrence of environmental pollution because it uses no chlorosilane, and the construction and operation of equipment are safe and convenient.

DISCLOSURE

Technical Problem

It is an object of the present invention to improve a method of producing high-purity silicon for solar cells using the conventional metallurgical technology developed for economic reasons and to provide an apparatus and method of producing high-purity polysilicon for solar cells using a more economic metallurgical technology.

Technical Solution

In order to accomplish the above object, the present invention provides a method of producing silicon for solar cells by a metallurgical process, the method comprising: a step of reduction in an arc furnace, consisting of introducing a silicon raw material into an arc melting furnace and smelting silicon of the introduced silicon raw material with carbon; a step of refining step by slag consisting of subjecting the reduced silicon to slag refining in a slag refining apparatus connected continuously to the arc melting furnace; a step of refining by unidirectional solidification consisting of unidirectionally solidifying the slag-refined silicon; and a step of steam plasma-electromagnetic continuous refining consisting of introducing the unidirectionally solidified silicon into a crucible surrounded by an induction coil and treating the introduced solidified silicon with a steam plasma torch while melting the solidified silicon.

In the method of the present invention, the slag-refined silicon is preferably introduced into the crucible for unidirectional solidification in a molten state so that the slag refining step and the unidirectional solidification refining step are continuously performed.

In the method of the present invention, the unidirectional solidification refining step is preferably performed while heating sources provided near the top, upper lateral portion and lower lateral portion of the crucible, respectively, are moved vertically with respect to the crucible.

In the method of the present invention, phosphorus (P) and boron (B) in the molten silicon are removed by a plasma torch in the slag refining step.

In the method of the present invention, metal impurities are removed from the silicon in the unidirectional solidification refining step.

In the method of the present invention, phosphorus (P) and boron (B) in the molten silicon are removed using steam plasma in the steam plasma-electromagnetic continuous refining step.

Advantageous Effects

According to the present invention, a series of processes ranging metallurgical-grade silicon production employing an arc melting furnace to slag refining, unidirectional solidification refining and steam plasma are continuously performed, and thus the energy and time required for melting of a material introduced into each process can be reduced, thereby producing the production cost.

In addition, according to the present invention, chlorosilane is not emitted because a vapor phase process is not performed, and high-purity silicon can be produced without using an acid leaching process included in conventional metallurgical processes. Thus, the yield can be increased, and the consumption of energy and the occurrence of environmental pollution can be reduced.

BEST MODE

Hereinafter, the present invention will be described in detail with reference to the accompanying drawings, but the scope of the present invention is not limited to the drawings.

Figure 1:
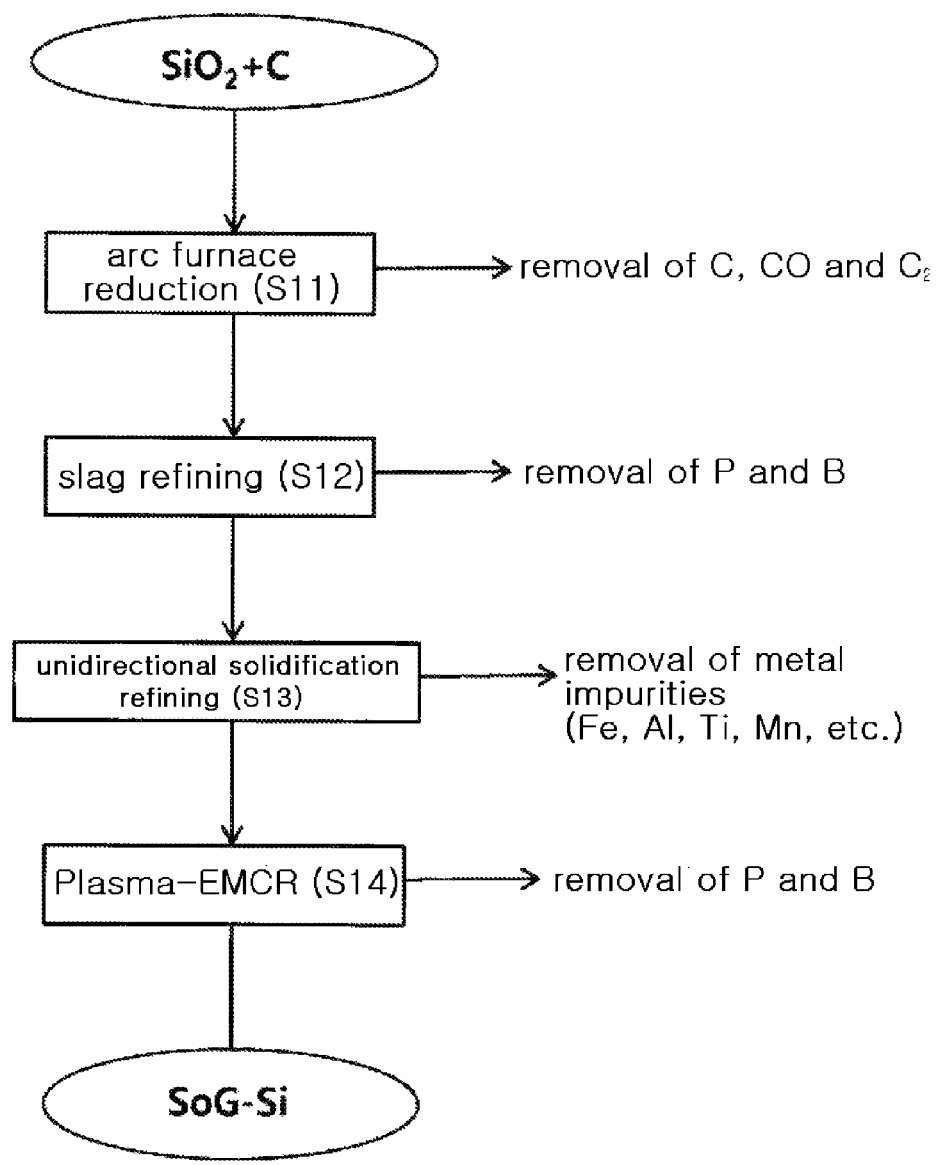
FIG. 1 is an overall process flowchart showing a method for producing silicon according to the present invention.

FIG. 1 is an overall process flowchart showing a method for producing silicon according to the present invention. As shown in FIG. 1, the method of the present invention comprises: (S11) a step of reduction in an arc furnace, consisting of removing C and CO in a silicon reduction atmosphere using silica stone and carbon black by an arc so as to produce metallurgical grade silicon; (S12) a step of refining by slag consisting of removing phosphorus (P) and boron (B) by slag; (S13) a step of refining by unidirectional solidification consisting of removing metal impurities (Fe, Al, Ti, Mn, etc.) by means of unidirectional solidification; and (S14) a step of steam plasma-electromagnetism continuous refining consisting of charging a furnace with the unidirectionally solidified silicon and removing boron (B) by a steam plasma torch.

With the arc furnace reduction step (S11), known processes of producing metallurgical-grade silicon from silica stone include a carbon reduction process employing an arc melting furnace, a plasma reduction process, a thermite process employing Al or the like, a self-propagating high-temperature synthesis (SHS) process employing Mg or the like. Among these processes, the carbon reduction process that is frequently used in the industrial production of metallurgical-grade silicon due its economic advantage is used in the present invention.

Figure 3:
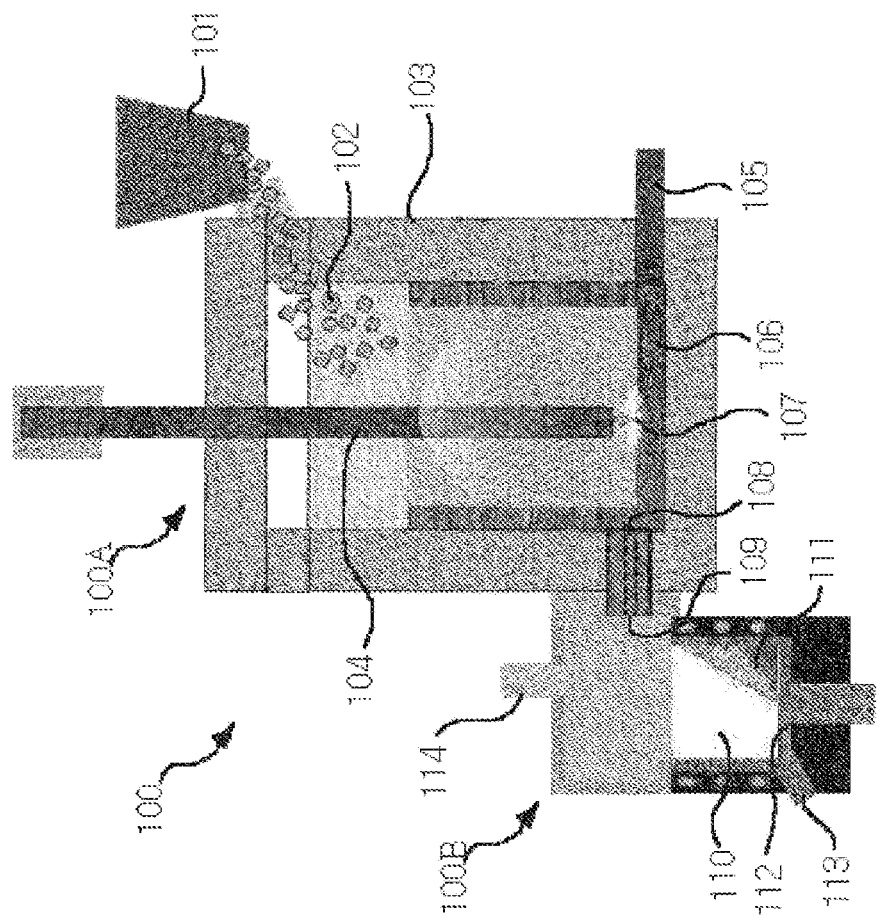
FIG. 3 shows an apparatus for continuously performing arc furnace reduction and slag refining according to the present invention.

An arc melting furnace is used in the present invention, because a temperature of 1,819° C. or higher is required to reduce $SiO_2$ with carbon to thereby produce Si. As shown in FIG. 3, a crucible in an arc melting furnace 100A that is used in the present invention is a crucible 106 having good thermal properties and can function as an electrode 107 when arc discharge occurs.

In the arc furnace reduction step (S11), raw materials including silica stone, coke, charcoal, wood chips and the like are used at various mixing ratios. Specifically, a mixture of raw materials 102 is introduced into a crucible 106, and electrodes 104 and 105 are moved in a power-on state to control the current and voltage of an arc. The current and voltage of the arc melting furnace 100A are controlled manually. At 2-4 hours after the occurrence of arc discharge 107, the timing of tapping is determined in view of the state of the high-temperature gas generated and the state of the introduced material. The voltage and current of the discharged arc 107 are maintained in the ranges of 20-65 V and 1500-2000 A, respectively. After first tapping, additional introduction of the raw material is performed, and after the current and voltage of the arc were stabilized, high-temperature gas discharge, additional introduction and second tapping are sequentially performed.

Silicon tapped from the arc melting furnace 100A after the arc furnace reduction step S11 shows a purity of about 99.8%.

The present invention is characterized in that metallurgical-grade silicon tapped from the arc melting furnace 100A is not discharged to the outside and is subjected directly to a slag refining process without being solidified after the arc furnace reduction process, because the arc melting furnace 100A is connected with a slag refining apparatus 100B to provide an arc reduction/slag refining apparatus 100.

FIG. 3 shows the arc reduction/slag refining apparatus 100 in which molten metallurgical-grade silicon produced in the arc melting furnace 100A can be moved directly to the slag refining apparatus 100B and can be subjected to slag refining.

The slag refining step (S12) is performed using $SiO_2$—CaO—CaF-based slag in an apparatus in which the metallurgical-grade silicon and the slag are melted. First, atmospheric gas in the slag refining apparatus 100B is controlled to a reducing gas atmosphere. Specifically, the atmosphere in the slag refining apparatus 100B is controlled to a reducing gas atmosphere consisting of at least one inert gas selected from among Ar and He and at least one reducing gas selected from $H_2$ and $CH_4$. Then, the metallurgical-grade silicon (MG-Si) and the slag are introduced into the crucible controlled to the reducing gas atmosphere.

In the present invention, it is required that the metallurgical-grade silicon (MG-Si) and the slag 110 should be introduced at a weight ratio of 1:1-3. If the amount of slag introduced is too small relative to the amount of metallurgical-grade silicon introduced, the molten silicon can be incorporated into the slag in a subsequent melting process, because the difference in specific gravity between the metallurgical-grade silicon and the slag is small. If the slag is introduced in an excessive amount, the refining process is cost-ineffective. More preferably, the metallurgical-grade silicon (MG-Si) and the slag are introduced at a weight ratio of 1:2.

Next, the crucible 112 in the slag refining apparatus is heated to melt the introduced metallurgical-grade silicon and slag, so that phosphorus (P) in the molten silicon is removed into the slag in the form of phosphide ($P^{3-}$) ions by an interfacial reaction between the molten silicon and slag. Herein, the crucible 112 is preferably heated to a temperature of 1450-1600° C.

In other words, phosphorus (P) in the silicon is moved toward the slag by controlling the partial pressure of oxygen through a reduction/refining reaction in a hydrogen atmosphere. More specifically, the present invention is based on a concept in which phosphorus (P) in the metallurgical-grade silicon is separated and removed by changing the ionic stability of phosphorus (P) of the slag through control of the equilibrium partial pressure of oxygen at the interface between the molten silicon and slag in the refining process.

In the unidirectional solidification refining step (S13), metal impurities (Fe, Al, Ti, Mn, etc.) are removed. In a unidirectional solidification refining apparatus according to the prior art, a solidification process is performed using a single lateral heater, and for this reason, it is impossible to control the temperature of various regions of the solidified interface, and thus impurities at the solidified interface are not easily moved to the liquid-phase region, making it difficult to efficiently produce high-purity silicon.

Figure 4:
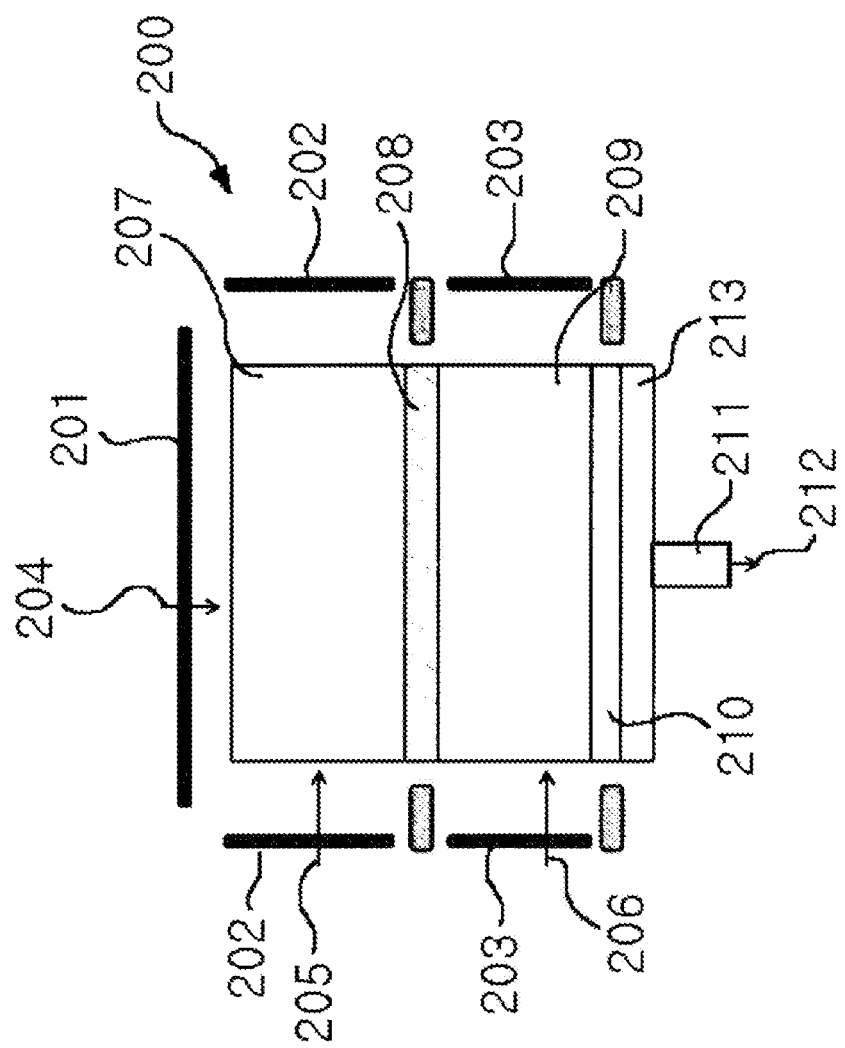
FIG. 4 is a conceptual view schematically illustrating a unidirectional solidification refining apparatus according to the present invention.

However, as shown in FIG. 4, a unidirectional solidification 200 according to the present invention comprises: a chamber having a hollow structure and provided with a heat insulation material for heat insulation from the outside; a support on which a crucible containing a silicon material is placed in the chamber; an upper heater 201 placed above the crucible in the chamber so as to provide heat to the crucible; a lateral upper heater 202 and a lateral lower heater 203, which are placed around the crucible in the chamber so as to provide heat to the crucible and are separated from each other vertically; a heat exchanger 211 provided at the side of the support so as to cool the bottom of the crucible; and a moving device configured to vertically move the chamber together with the lateral upper heater 202 and lateral lower heater 203 of the chamber according to the position of a solidified interface 208 between a solidification region 209 and a melting region 207 in the crucible in a state in which the position of the crucible is fixed to the support. Thus, in comparison with the conventional solidification refining apparatus comprising a single integrated lateral heater, the unidirectional solidification apparatus 200 according to the present invention has a characteristic in that the lateral upper heater 202 and the lateral lower heater 203 can be separately controlled. By virtue of this characteristic, convection in the liquid phase can be activated, so that impurities separated from the silicon solid phase can be prevented from being excessively deposited around at the solidified interface 208, thereby further increasing the degree of refining of the silicon.

The unidirectional solidification apparatus 100 that is used in the unidirectional solidification refining step (S13) is described in further detail in Korean Patent Application No. 2011-0068049 filed in the name of the present inventors.

Figure 5:
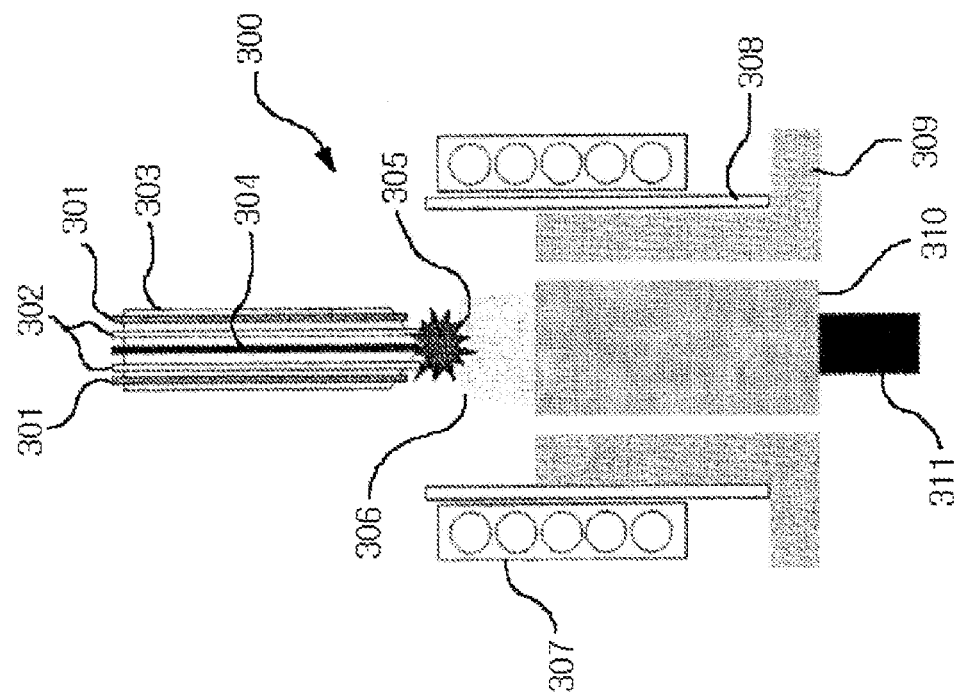
FIG. 5 schematically shows a steam plasma-electromagnetic continuous refining apparatus according to the present invention.

In the steam plasma-electromagnetic continuous refining step (S14), boron (B) in the silicon is removed using a material that reacts with boron (B) under a certain pressure while phosphorus (P) is removed, and as shown in FIG. 5, the silicon is heated by an induction coil 307 to make a silicon melt 306, after which impurities in the silicon are removed by directional solidification. Preferably, the silicon melt 306 does not come into contact with the inner wall surface of the crucible 309.

The reason why the silicon melt 306 cannot come into contact with the inner wall surface of the crucible 309 is that the application of an alternating current to the crucible 309 by the induction coil 307 induces a change in the magnetic field to form an induced current on the silicon in the crucible 309, and the silicon in the crucible 309 is melted by Joule's heat generated from the induced current, and the silicon melt 306 is directed to the inside of the crucible 309 by the Lorentz force, and thus does not come into contact with the inner wall surface of the crucible 309. Even when the direction of the current changes, the direction of the magnetic field also changes in the same manner, and thus the Lorentz force is always directed to the inside of the silicon melt 306. Because the silicon melt 306 does not contact with the inner wall surface of the crucible 309 as described above, impurities on the crucible 309 do not penetrate into the silicon melt 306, and the crucible 309 can be reused.

During the steam plasma-electromagnetic continuous refining step (S14), a boron-removing material that reacts with boron (B) under a certain pressure is injected into the crucible to remove boron (B). Also, because phosphorus (P) has high vapor pressure, the pressure in the apparatus is reduced to atmospheric pressure or below so that phosphorus (P) is removed by evaporation.

Boron (B) is removed by reacting it with a material that reacts with boron. Typical examples of the material that reacts with boron include $H_2$, $O_2$, $H_2O$ or plasma gas ions. For example, boron (B) can be removed in the form of HBO gas by reaction with $H_2O$ gas. However, because silicon is also reactive with $H_2O$ gas, SiO gas and $SiO_2$ are produced.

$SiO_2$ is produced by a reaction between SiO gas produced and $O_2$ of $H_2O$ gas, and SiO gas and $O_2$ gas have good reactivity and react with each other within a short time, and for this reason, SiO gas is discharged into air, $SiO_2$ is immediately produced. In addition, SiO gas molecules react with each other so that they are decomposed into $SiO_2$ and Si. In other words, when SiO gas is produced, $SiO_2$ will inevitably be produced.

$SiO_2$ produced as described above will adhere to the crucible to interfere with heating or will adhere to other parts to reduce the purity of the silicon. In addition, because $SiO_2$ has a density lower than that of the molten liquid silicon, it will float on the molten liquid silicon and interfere with the reaction of boron (B)-reactive gas such as $H_2O$ gas with boron in the silicon to thereby reduce the removal rate of boron (B).

For this reason, it is required to prevent the production of $SiO_2$, which occurs when boron (B) is removed during the production for high-purity silicon for solar cells. According to thermodynamic calculations, a reverse reaction of the above-described reaction occurs at a temperature of 1870° C. or higher under a pressure of 1 atm. In other words, $SiO_2$ reacts with Si to produce SiO gas and is decomposed into SiO gas and $O_2$ even in the presence of $O_2$ gas. Thus, when the temperature of the crucible is maintained at 1870° C. or higher under a pressure of 1 atm, the influence of $SiO_2$ can be reduced. In addition, as the temperature of the crucible increases, the reactivity of $H_2O$ gas with boron (B) increases and the reactivity of $H_2O$ with silicon decreases. In conclusion, the removal rate of boron (B) can be increased by increasing the reaction temperature. In one embodiment, the removal rate of boron (B) can be effectively increased by reacting Si with $H_2O$ using a high-temperature plasma torch.

According to the thermoplastic laws, a reduction in the reaction pressure shows the same effect as that of an increase in the reaction temperature, and thus a reduction in the reaction pressure is also the way to increase the removal rate of boron (B) and prevent the production of $SiO_2$. When the reaction pressure is reduced to 1 atm or lower, the production of $SiO_2$ can be inhibited even at a temperature of 1870° C. or lower. In addition, a reduction in the reaction pressure as described above is advantageous for the removal of not only boron (B), but also phosphorus (P).

Mode for Invention

The present inventors have established the most suitable refining conditions that can maximize the ability to remove phosphorus (P), boron (B) and other metal impurities by a continuous process comprising an arc furnace reduction step (S11), a slag refining step (S12), a unidirectional solidification refining step (S13) and a steam plasma-electromagnetic continuous refining step (S14), as shown in FIG. 1.

The slag refining step (S12) is a refining process for mainly removing phosphorus (P) and boron (B) from silicon. For removal of phosphorus (P) and boron (B), an element such as calcium (Ca) is required to be added, and for this reason, an additional refining process for removing this added element is required. Thus, the method of the present invention comprises the unidirectional solidification refining step (S13) and the steam plasma-electromagnetic continuous refining step (S14), which are continuously performed following the slag refining step (S12).

In an example of the present invention, in order to examine the amounts of phosphorus (P) and boron (B) that are removed by the slag refining step (S12), the slag refining step (S12) alone was performed, and the concentrations of P and B before and after the slag refining step and the removal rates thereof are shown in Table 1 below.

TABLE 1

| S12 | Silicon source | Initial concentration (ppm) | Concentration after refining (ppm) | Removal rate (%) |
|---|---|---|---|---|
| P | UMG-Si (comprising phosphorus added thereto) | 3000 | 332.9 | 88.9 |
| B | P-type Si wafer | 350 | 91 | 74 |

In the example shown in Table 1 above, the slag-refining step (S12) was performed using UMG-Si (upgraded metal grade silicon) and a P-type Si wafer as a silicon source. In order to clearly examine the removal rate of phosphorus (P), the concentration of phosphorus (P) before refining was adjusted to 3000 ppm by artificially adding phosphorus (P) to UMG-Si, and the concentration of boron (B) in the P-type Si wafer before refining was 350 ppm. After the slag refining step (S12), UMG-Si showed a phosphorus (P) concentration of 332.9 ppm corresponding to a phosphorus (P) removal rate of about 88.9%, and the P-type Si wafer showed a boron (B) concentration of 91 ppm corresponding to a boron (B) removal rate of about 74%.

The unidirectional solidification refining step (S13) is mainly intended to remove metal impurities (Fe, Al, Ti, Mn, etc.) from silicon.

Table 2 below shows the concentrations of metal impurities, measured after performing the unidirectional solidification refining step (S13) alone. In the example shown in Table 2, unidirectional solidification refining was performed using UMG-Si (Upgraded Metal Grade Silicon) as a silicon source. Metal impurities were best removed under the conditions of temperature gradient of 300° C. and ingot growth rate of 0.5 mm/min, and the results of ICP-MS analysis of major impurities are shown in Table 2 below.

TABLE 2

|   | B (ppm) | Na (ppm) | Mn (ppm) | Al (ppm) | K (ppm) | Ca (ppm) | Ti (ppm) | Ge (ppm) | Fe (ppm) | Purity (%) |
|---|---|---|---|---|---|---|---|---|---|---|
| S13 | 1.33 | 0.027 | 0.03 | 0.869 | 0 | 0.268 | 0 | 0.535 | 1.801 | 99.9995 |

As can be seen in Table 2 above, most metal impurities were significantly removed, and the purity of the resulting silicon was 99.999% corresponding to a 5N grade. The problem that the concentration of boron (B) among impurities is somewhat high can be resolved by the steam plasma-electromagnetic continuous refining step (S14).

The steam plasma-electromagnetic continuous refining step (S14) is mainly intended to remove and minimize phosphorus (P) and boron (B) from silicon.

In the example shown in Table 3 below, the steam plasma-electromagnetic continuous refining step (S14) alone was performed, and the experiment was focused on the optimization of experimental conditions in order to preferentially remove boron (B). The flow rate of argon gas was set at 10 L/min, the refining time was set at 10 minutes, and the flow rates of $H_2O$ and $H_2$ were controlled to 20-40 mL/min and 0.3-1.0 mL/min, respectively. The concentration of boron (B) after the experiment was analyzed by ICP-MS, and as a result, it could be seen that increases in the flow rates of $H_2O$ and $H_2$ led to an increase in the removal rate of boron (B).

TABLE 3

| Ar (l/min) | $H_2$ (ml/min) | $H_2O$ (ml/min) | time (min) | Boron concentration (ppm) |
|---|---|---|---|---|
| 10 | 20 | 0.3 | 10 | 0.9 |
| 10 | 20 | 0.5 | 10 | 1 |
| 10 | 20 | 1.0 | 10 | 0.7 |
| 10 | 30 | 0.3 | 10 | 1.7 |
| 10 | 30 | 0.5 | 10 | 0.46 |
| 10 | 30 | 1.0 | 10 | 0.36 |
| 10 | 40 | 0.3 | 10 | 0.48 |
| 10 | 40 | 0.5 | 10 | 0.17 (removal rate of 94%) |

As can be seen in Table 3 above, at a $H_2O$ flow rate of 0.5 ml/min and a $H_2$ flow rate of 40 ml/min, the concentration of boron (B) was reduced to 0.17 ppm, which corresponds to a boron (B) removal rate of 94% after performing the steam plasma-electromagnetic continuous refining step (S14). From such results, the flow rates of $H_2O$ and $H_2$, most suitable for removal of boron (B), could be determined. This concentration of boron (B) in silicon decreased by about 94% from 2.9 ppmw to 0.17 ppmw. Table 3 above shows the experimental conditions used to examine the effect of $H_2O+H_2$ in the steam plasma-electromagnetic continuous refining step (S14) and the results of removal of boron (B).

Table 4 below the concentrations of major components, measured after sequentially performing the arc furnace reduction step (S11), the slag refining step (S12), the unidirectional solidification refining step (S13) and the continuous steam plasma-electromagnetic refining step (S14) according to the present invention.

TABLE 4

|   | B (ppm) | Mg (ppm) | Al (ppm) | P (ppm) | Ca (ppm) | Ti (ppm) | Ge (ppm) | Fe (ppm) | Purity (%) |
|---|---|---|---|---|---|---|---|---|---|
| S11 | 15.5 | 5.2 | 478.4 | 57.9 | 331.7 | 635.5 | 1.6 | 2885 | 99.5 |
| S11 + S12 | 2.9 | 0.2 | 16.34 | 4.2 | 1.3 | 0 | 1.44 | 0.07 | 99.995 |
| S11 + S12 + S13 | 1.5 | 0.02 | 1.3 | 6.3 | 0.1 | 0.01 | 0.78 | 0.1 | 99.999 |
| S11 + S12 + S13 + S14 | 0.83 | 0.1 | 0 | 2.86 | 0.1 | 0.1 | 0.5 | 0 | 99.999 |

As can be seen in Table 4 above, after the arc furnace reduction step (S11), the concentration of boron (B) or phosphorus (P) was somewhat high even after performing the slag refining step (S12), but the concentrations of other impurities were significantly reduced. Then, boron (B) and phosphorus (P) together with other metal impurities were significantly removed by the unidirectional solidification refining step (S13) and the steam plasma-electromagnetic continuous refining step (S14). The final purity of silicon approached a 6N grade, suggesting that high-purity silicon suitable for use in solar cells can be produced by the optimum refining process.

Figure 2:
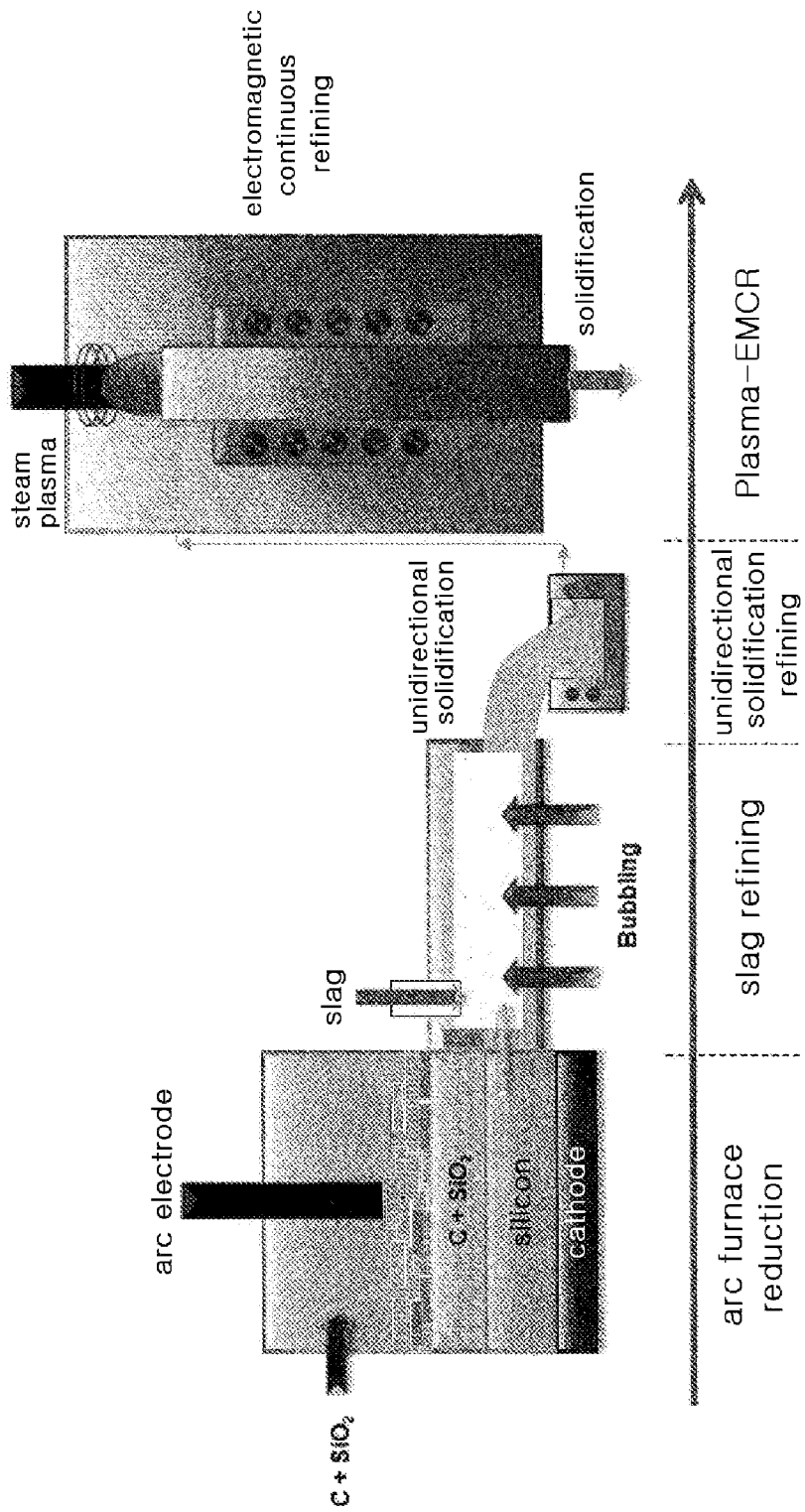
FIG. 2 is a schematic view showing the overall process for producing silicon according to the present invention.

FIG. 2 schematically shows an overall process of the present invention. As shown in FIG. 2, the apparatus of producing silicon for solar cells using a metallurgical process comprises an arc reduction/slag refining apparatus 100, a unidirectional solidification refining apparatus 200, and a steam plasma-electromagnetic continuous refining apparatus 300. In the present invention, the most suitable refining conditions that can maximize the removal of impurities were established.

FIG. 3 shows an arc reduction/slag refining apparatus 100 comprising an arc melting furnace 100A connected with a slag refining apparatus 100B. The arc melting furnace 100A comprises an electromagnetic induction melting crucible 106, a raw material supply unit 101 disposed at the upper side of the crucible 106, arc electrodes 104 and 105 disposed in the crucible 106 and serving to cause arc discharge 107, and a tapping unit 108 disposed at the lower side of the crucible 16. The tapping unit 108 of the arc melting furnace communicates with a molten silicon introduction unit 109 that is connected with the slag refining apparatus 100B, and thus the arc reduction process in the arc melting furnace 100A and the slag refining process in the slag refining apparatus 100B can be continuously performed. The slag refining apparatus 100B comprises: a slag refining crucible 112 disposed at one side of the crucible 106 of the arc reduction furnace; a molten silicon introduction unit 109 provided at one upper side of the slag refining crucible 112; a plasma torch disposed at the top of the slag refining crucible 112; and a high-purity silicon tapping unit 113 provided at the side of the lower portion of the slag refining crucible 112.

The processes that are performed in the arc reduction/slag refining apparatus 100 will now be sequentially described with reference to FIG. 3. First, a raw material 102 is introduced through a raw material supply unit 101, and arc discharge 107 occurs between an electrode 104 and an electrode 105 to melt the raw material 102. The raw material 102 is composed of silica stone, coke, charcoal, and wood chips, and the $SiO_2$ and carbon (C) components of the raw material react with each other to form silicon carbide (SiC) in the upper portion of the arc melting furnace 100A and silicon (Si) in the lower portion. The molten silicon (Si) formed in the lower portion is not solidified and moves along the tapping unit 108 of the arc melting furnace to the molten silicon introduction unit 109 and subjected to slag refining.

The plasma torch 114 disposed at the top of the slag refining apparatus 100B can assist in maintaining the tapped metallurgical-grade silicon in a molten state in the molten silicon introduction unit 109, can maintain the metallurgical-grade silicon in a molten state until the silicon is discharged through the high-purity silicon tapping unit 113. Also, the plasma torch 114 enables high-purity silicon to be more efficiently produced by plasma refining. Slag is added to the metallurgical-grade silicon introduced into the molten silicon introduction unit 109 of the slag refining apparatus 100B, and the mixture of the slag and the metallurgical-grade silicon 110 is subjected to a slag refining process. After completion of the slag refining process, the silicon is discharged through the high-purity silicon tapping unit 113.

FIG. 4 schematically shows the principle of the unidirectional solidification refining apparatus according to the present invention. The unidirectional solidification refining apparatus 200 comprises: a crucible 210 capable of receiving silicon therein; a cooling plate 213 disposed below the crucible 210 and capable of cooling silicon; a heat exchanger 211 disposed below the cooling plate 213; an upper heater 201 disposed above the crucible 210; and a lateral upper heater 202 and a lateral lower heater 203, which surround the crucible 210 and can be moved vertically with respect to the crucible 210.

The upper heater 201 is configured to supply heat to the crucible 201, and the lateral upper heater 202 and the lateral lower heater 203 disposed below the lateral upper heater 202 are placed around the crucible 210 to form a cylindrical structure and configured to supply heat to the crucible 210. Herein, the lateral upper heater 202 together with the upper heater 201 functions to melt the silicon material contained in the crucible 210, and the lateral lower heater 203 functions to heat the solidified material at a temperature equal to or lower than the melting temperature of the solidified material.

The heat exchanger 211 is placed below the cooling plate 213 and configured to unidirectional solidification sequentially from the bottom to the top in order to cool the bottom of the crucible 210.

The unidirectional solidification refining process will now be sequentially described. First, after completion of the slag refining process, the silicon is introduced into the crucible 210. Herein, the silicon may be introduced into the unidirectional solidification refining apparatus 200 subsequently to the slag refining process in a molten state or may be introduced into the unidirectional solidification refining apparatus 200 in a solidified state after the slag refining process. The upper heater 201 and the lateral upper heater 202 are operated to maintain the silicon material in the crucible in a molten state or to melt the silicon material. This process of melting the silicon material is preferably performed in an atmosphere of inert gas such as Ar or a vacuum atmosphere.

When the melting of the silicon material by the above-described process is completed, the molten silicon in the crucible is solidified upward using the heat exchanger 211 below the crucible 210. The molten silicon in the crucible 210 is solidified gradually from the bottom to the top. This solidification is performed while the heaters are moved upward in such a manner that the upper end of the lateral lower heater is gradually elevated along the solidified interface 208. Because the solidified interface 208 is controlled to the upper end of the lateral lower heater 202, the mixed region of the solid phase and the liquid phase in the unidirectional solidification refining process can be easily controlled, and thus the temperature gradient of the solid phase and the liquid phase can be easily controlled so that the diffusion of impurities to the liquid phase can be facilitated, thereby increasing the removal rate of impurities.

FIG. 5 schematically shows the configuration of a steam plasma-electromagnetic continuous refining apparatus according to the present invention. As shown therein, the steam plasma-electromagnetic continuous refining apparatus 300 comprises a crucible 309, an induction coil 307 wound around the crucible 309, and a steam plasma torch disposed at the top of the crucible 309, and is configured such that silicon is introduced into the crucible 309 and melted by electromagnetic induction.

The steam plasma-electromagnetic continuous refining process will now be sequentially described. First, the silicon to be purified is introduced into the crucible 309 and then heated by the induction coil 307 to make a silicon melt 306. Due to the Lorentz force acting on the silicon melt 306, the silicon melt 306 does not come into contact with the inner wall of the crucible 309. In this state, $O_2$, $H_2$, $H_2O$, $N_2$ or the like that is a material for removing boron is introduced through a gas inlet 301. The boron-removing material may be introduced together with an inert material such as Ar or He, which is introduced through an inert material inlet 302. While the boron-removing material is introduced together with the inert material, gas in the crucible is forcibly discharged to the outside using a pump or the like so as to control the internal pressure of the crucible to a specific level. Herein, the internal pressure is atmospheric pressure or lower. In addition, gas may also be discharged between the crucible 309 and the silicon melt 306/silicon ingot 310 without using a pump or the like. Convection current occurs in the silicon melt due to the Lorentz force so that the boron-removing material comes into contact with the whole of the silicon melt, and as a result, boron is removed by gasification.

Herein, the boron-removing material is introduced in a plasma or gas state. Plasma is more preferably used as the boron-removing material, because the temperature of gas can be increased to prevent the temperature of the silicon melt from decreasing and to increase the reaction temperature. When the temperature of the silicon melt 306 is slowly reduced while the boron-removing material and the silicon to be refined are continuously introduced, the silicon melt 306 is cooled to form a silicon ingot 310. When the silicon melt is cooled to form solid silicon, impurities in low-purity silicon are pushed out to the liquid phase due to the difference in solubility between the solid silicon and impurities in the liquid silicon, and thus high-purity silicon can be obtained.

While the present invention has been described with reference to the particular illustrative embodiments, it will be understood by those skilled in the art to which the present invention pertains that the present invention may be embodied in other specific forms without departing from the technical spirit or essential characteristics of the present invention. Therefore, the embodiments described above are considered to be illustrative in all respects and not restrictive. Furthermore, the scope of the present invention is defined by the appended claims rather than the detailed description. In addition, it should be understood that all modifications or variations derived from the meanings and scope of the present invention and equivalents thereof are included in the scope of the appended claims.

DESCRIPTION OF THE REFERENCE NUMERALS IN THE DRAWINGS

100: arc reduction and slag refining apparatus;
100A: arc melting furnace;
100B: slag refining apparatus;
101: raw material supply unit;
102: raw material; 103: refractory material;
104: electrode; 105: electrode;
106: crucible; 107: arc discharge;
108: arc melting furnace tapping unit;
109: molten silicon introduction unit;
110: slag and metallurgical-grade silicon;
111: Gas bubbling; 112: crucible;
113: high-purity silicon tapping unit;
114: plasma torch;
200: unidirectional solidification refining apparatus;
201: upper heater; 202: lateral upper heater;
203: lateral lower heater;
204: direction of movement of heat from upper heater;
205: direction of movement of heat from lateral upper heater;
206: direction of movement of heat from lateral lower heater;
207: melting region; 208: solidified interface;
209: solidification region;
210: crucible; 211: heat exchanger;
212: direction of movement of emitted heat;
213: cooling plate;
300: steam plasma-electromagnetic continuous refining apparatus;
301: gas inlet; 302: inert material inlet;
303: steam plasma torch; 304: electrode;
305: arc discharge; 306: silicon melt;
307: induction coil; 308: quartz;
309: crucible; 310: silicon ingot;
311: electrode.

The invention claimed is:

1. A method of producing silicon for solar cells by a metallurgical process, the method comprising:
   a step of reduction in an arc furnace, consisting of introducing a silicon raw material into an arc melting furnace and smelting silicon of the introduced silicon raw material with carbon;
   a step of refining step by slag consisting of subjecting the reduced silicon to slag refining in a slag refining apparatus connected continuously to the arc melting furnace;
   a step of refining by unidirectional solidification consisting of unidirectionally solidifying the slag-refined silicon; and
   a step of steam plasma-electromagnetic continuous refining consisting of introducing the unidirectionally solidified silicon into a crucible surrounded by an induction coil and treating the introduced solidified silicon with a steam plasma torch while melting the solidified silicon.

2. The method of claim 1, wherein the slag-refined silicon is introduced into the crucible for unidirectional solidification in a molten state so that the slag refining step and the unidirectional solidification refining step are continuously performed.

3. The method of claim 1, wherein the unidirectional solidification refining step is performed while heating sources provided near a top, upper lateral portion and lower lateral portion of the crucible, respectively, are moved vertically with respect to the crucible.

4. The method of claim 1, wherein phosphorus (P) and boron (B) in the molten silicon are removed by a plasma torch in the slag refining step.

5. The method of claim 1, wherein metal impurities are removed from the silicon in the unidirectional solidification refining step.

6. The method of claim 1, wherein phosphorus (P) and boron (B) in the molten silicon are removed using steam plasma in the steam plasma-electromagnetic continuous refining step.

* * * * *